United States Patent [19]
Liu et al.

[11] Patent Number: 5,844,241
[45] Date of Patent: Dec. 1, 1998

[54] SYSTEM AND METHOD FOR DETERMINING INTERNAL RADIOACTIVITY AND ABSORBED DOSE ESTIMATES

[75] Inventors: An Liu, Diamond Bar; Lawrence E. Williams, Arcadia; Andrew Raubitschek, San Francisco, all of Calif.

[73] Assignee: City of Hope, Duarte, Calif.

[21] Appl. No.: 684,179

[22] Filed: Jul. 19, 1996

[51] Int. Cl.$^6$ .................................................. G01T 1/161
[52] U.S. Cl. ........................................................ 250/363.04
[58] Field of Search ........................ 250/363.04, 363.05; 378/901

[56] References Cited

U.S. PATENT DOCUMENTS 5,391,877   2/1995   Marks ................................ 250/363.04

OTHER PUBLICATIONS

S. R. Thomas et al., "In Vivo Quantitation of Lesion Radioactivity Using External Counting Methods, "*Med. Phys.*, Vol. 3, No. 4, pp. 253–255 (1976).

S. R. Thomas et al., "Quantitative External Counting Techniques Enabling Improved Diagnostic and Therapeutic Decisions in Patients With Well–Differentiated Thyroid Cancer," *Radiology*, vol. 122, pp. 731–737 (1977).

T.K. Johnson and R.L. Vessella, "On the Possibility of 'Real Time' Monte Carlo Calculations for the Estimation of Absorbed Dose in Radioimmunotherapy," *Computer Methods and Programs in Biomedicine.*, vol. 29, pp. 205–210 (1989).

T.K. Johnson and S.B. Colby, "Photon Contribution to Tumor Dose from Considerations of $^{131}$I Radiolabeled Antibody Uptake in Liver, Spleen and Whole Body,"*Med. Phys.*, vol. 20(6), pp. 1667–1674 (1993).

G. Sgouros, et al., "Three–Dimensional Dosimetry for Radio Immunotherapy Treatment Planning," *J. Nucl. Med.* vol. 34, pp. 1595–1601 (1993).

M.L. Goris, S.A. Knox, K.R. Nielsen, O. Bouillant, "Organ Modeling in the Quantitation of Planar Images for Distribution Studies," *Cancer* 73(3); pp. 919–922 (1994).

M.J. Berger, "Distribution of Absorbed Dose Around Point Sources of Electrons and Beta Particles in Water and Other Media," MIRD Pamphlet No. 7, *Nucl. Med.*, vol. 12: Supl. No. 5, pp. 5–24 (1971).

W.V. Prestwich, J. Nunes, and C.S. Kwok, "Beta Dose Point Kernels for Radionuclides of Potential Use in Radio Immunotherapy," *J. Nucl. Med.*, vol. 30, pp. 1036–1046 (1989).

*Primary Examiner*—Constantine Hannaher
*Attorney, Agent, or Firm*—Rothwell, Figg, Ernst & Kurz

[57] ABSTRACT

A system and method determines internal radioactivity and absorbed dose estimates of a patient more accurately and with greater ease. Internal radioactivity is determined by the CAMI (CT scan Assisted Matrix Inversion) system and method which uses uptake information from the gamma camera images and anatomic data from CT (Computerized Tomography) scans. Absorbed dose estimates are obtained by the MAVSK (Monte Carlo Assisted Voxel Source Kernel) system and method which uses a MCNP (Monte Carlo program for electron and photon transport) to simulate a voxel source kernel for $^{90}$Y analogous to a point source function.

9 Claims, 8 Drawing Sheets

Anterior　　Posterior　　Anterior
FIG.8A　　FIG.8B　　FIG.8C

SYSTEM AND METHOD FOR DETERMINING INTERNAL RADIOACTIVITY AND ABSORBED DOSE ESTIMATES

GOVERNMENT RIGHTS STATEMENT

This invention was made with government support under Grant Nos. P01 143904, 33527, and 43904 awarded by the National Institutes of Health. The government has certain rights in the invention.

BACKGROUND OF THE INVENTION

1. Field of the Invention

The present invention relates to a system and method for determining internal radioactivity and absorbed dose estimates of a patient. More specifically, the present invention determines internal radioactivity uptake in a patient who is given a radiopharmaceutical or other radioactive carrier by using a CT scan assisted matrix inversion (CAMI) method, and the present invention also estimates radiation dose received by a patient by using a Monte Carlo assisted voxel source kernel (MAVSK) method.

2. Background and Related Art

Radiology consists of several major divisions including diagnostic radiology, therapeutic radiology, and special radiologic imaging systems. Whereas the main function of the diagnostic radiologist is to produce and interpret images of internal organs of the body using radiation, therapeutic radiology concerns itself primarily with the treatment of disease by the destruction of diseased tissue with high-energy radiation. Special imaging radiology includes nuclear techniques, computerized tomography (CT), and ultrasound.

In nuclear medicine, radiation is usually internally distributed in the body and arises from the decay of radioactive materials which a patient receives (e.g., by injection, inhalation, or ingestion). An important application is organ imaging, in which the patient receives a gamma-emitting radioisotope that accumulates in an organ (or conversely, the exclusion of an isotope from a particular organ).

Pathological lesions, variations in blood perfusion or anatomical variations will produce an abnormal accumulation (or exclusion) of the isotope in particular organs. Accordingly, mapping the distribution of the isotope by detecting the emitted gamma rays yields an image which provides clues of the presence of pathological lesions.

Mapping the time distribution of the radioisotope image usually requires following the activity over one or several selected areas. Devices for this include the simplest types of radiation detector systems (probes) or gamma cameras which generally use scintillation crystals because they are the most efficient for gamma detection.

The basic configuration of such a probe generally consists of a collimator to limit the field of view, followed by a scintillator, which in turn is followed by a photomultiplier with associated electronics for recording. Output curves are handled in many ways, such as by use of oscilloscope display, scalers, count-rate meters, or strip-chart recorders.

In computerized tomography, a very narrow x-ray beam is passed through the body in a plane perpendicular to the axis of the body. Total attenuation of the beam is then measured by a detector. This measurement is repeated thousands of times with different rays across the body in the same plane to obtain thousands of attenuation measurements across a narrow slice of the body in a plane perpendicular to the axis.

The attenuation of a narrow beam along a path can be expressed as a product of the attenuation through each segment of that path. Since the attenuation is exponential, the total attenuation argument $\mu x$ can be expressed as the sum of the individual arguments for each segment:

$$\mu x = \mu_1 x_1 + \mu_2 x_2 + \mu_3 x_3 + \ldots + \mu_n x_n$$

With this concept, one can envision a CT slice as being composed of a number of small volume elements, called voxels. Each measurement of the attenuation of the narrow beam across a slice is thus a measurement of the attenuation of those voxels in the path of that measurement. Accordingly, it is possible to set up a set of linear equations for the solution to the attenuation in each voxel element.

In clinical and experimental radioimmunoimaging and radioimmunotherapy (RIT), knowledge of the absorbed radiation dose in normal tissue and in tumors is very important for an understanding of normal tissue toxicity and tumor dose response. For example, the dose due to monoclonal antibodies (Mabs) is calculated rather than measured from radioactive content of the tissues. Absolute radioactivity distributions are usually calculated from some non-invasive imaging procedures. The gamma camera is a non-invasive method currently available to assess normal organ and tumor biodistribution of radiolabeled antibodies.

Conventional methods of calculating internal radioactivity have various limitations. For example, although some investigators believe that quantitative single photon emission computer tomography (SPECT) will become the method of choice, it is currently difficult to implement and error-prone.

In the opposing view first developed by Thomas et al. (in "In Vivo Quantitation of Lesion Radioactivity Using External Counting Methods," *Med. Phys.*, Volume 3, pp. 253–255 (1976) and "Quantitative External Counting Techniques Enabling Improved Diagnostic and Therapeutic Decisions in Patients With Well-Differentiated Thyroid Cancer," *Radiology*, Volume 122, pp. 731–737 (1977)), regions of interest (ROIs), or the areas which may be medically significant, are drawn around each organ on both anterior and posterior planar gamma-camera scans. The total radioactivity in the organ is estimated by use of various information including the geometric mean of the anterior and posterior views of the pertinent area, an attenuation correction, a calibration factor of the camera, the radioactive counts per minute from the anterior and posterior views, and a buildup factor B.

More specifically, for a point source in the anterior projection:

$$C_A = A_O B(d) e^{-\mu d} CF; \tag{1a}$$

From the posterior projection:

$$C_P = A_O B(T-d) e^{-\mu(T-d)} CF \tag{1b}$$

where $\mu$=attenuation coefficient (cm$^{-1}$);

d=source depth measured from anterior surface (cm);

T=total patient thickness at the source position (cm);

B(x)=buildup factor (a depth (x) dependent parameter to account for phantom scatter. This factor was not used in Thomas' original work.)

$C_A$=counts per minute (cpm) in anterior gamma camera view;

$C_P$=cpm in posterior gamma camera view;

$A_O$=source radioactivity ($\mu$Ci);

CF=camera calibration factor (cpm/$\mu$Ci), measured with a source having a known amount of radioactivity.

Assuming the depth dependence of B(x) is very small, i.e., B(x)≅1, the source activity can then be calculated by taking the geometric mean of $C_A$ and $C_P$ such that:

$$A_O = \frac{(C_A C_P)^{1/2} e^{\mu T/2}}{CF} ; \quad (2)$$

For a volume source, the idea can be easily extended:

$$A_O = \frac{(C_A C_P)^{1/2} e^{\mu T/2}}{fCF} \quad (3)$$

The factor $f=2\sinh(\mu l/2)/(\mu l)$, where l is the thickness of the source, is due to the volume distribution of the radioactivity. When background activity exists, an ROI can be drawn near the source organ and background counts can be subtracted from the organ ROI counts on a pixel by pixel basis. Notice that only a single source organ is considered in this analysis and the correction for the contribution from background activity is only a first-order approximation.

However, with high background radioactivity and/or overlapping organs, it is difficult to draw ROI's around the organ, and the first-order background correction may not be accurate enough.

When organs are overlapping, it is impossible to separate the activity from different organs. For example, the liver overlaps the right kidney, and the kidney's activity densities are often too low to show up to allow accurate kidney ROI drawing.

Additionally, there is the problem of an organ or tumor being visible in only one view; e.g., the spleen or kidney from the posterior projection.

Furthermore, some organs are not visible in either anterior or posterior views; e.g., the kidneys at later time points after injection of Mabs. In such cases, the geometric mean is zero or close to zero and the opposing view method cannot be applied.

Thus, when the boundaries of organs do not show up very well on gamma camera images, supplemental scans may be necessary. For example, when the liver is imaged following the injection of $^{99m}$Tc-sulfur colloid, the lung is imaged with $^{99m}$Tc-macroaggregated albumin, or the kidney is imaged with $^{99m}$Tc-DTPA. These extra scans are used only for the outline of the normal organs and give extra radiation doses to the patient.

As noted above, radioactivity in the blood pool generally gives relatively high background tissue counts, especially at early time points.

In order to obtain absolute uptake in these cases, the present invention determines absolute uptake using uptake information from the gamma camera images and anatomic data from CT scans.

The absolute uptake may then be used to determine the absorbed dose received by the patient. In many radionuclide procedures, absorbed dose in various organs from sources within the body has to be estimated.

It is essential to determine the radiation dose in radioimmunotherapy where relatively large amounts of radioactivity are labeled onto anti-tumor antibodies and injected into the patient. The radionuclide is then transported to the tumor site(s) by the tumor specific antibody to deliver radiation dose to the tumor. Since a large amount of radioactivity is involved in this procedure, tumor dose as well as normal organ dose can no longer be just a crude estimation. Both absorbed doses have to be calculated in a more precise and systematic manner.

Conventional methods of absorbed dose estimation suffer from various shortcomings. The Medical Internal Radiation Dose (MIRD) Committee of the Society of Nuclear Medicine provides a general framework for the absorbed dose estimation of administered radiopharmaceuticals, and its most recent practical software implementation is the MIRDOSE3 program.

In MIRDOSE3, a uniform distribution of unit cumulated activities within each source organ is assumed. The average absorbed dose to a given target organ from a given source organ is then estimated by dividing the total energy deposited by the target organ mass (S factors).

This S matrix is calculated for several standard anatomic models (e.g., Standard Adult, Standard Adult Female, 15-year-old Phantom and several other models). The product of cumulated activity in a source organ and corresponding S factor gives the dose contribution from source to the target organ. Total target organ dose is then the summation of all source organ absorbed dose contributions.

There are several limitations with MIRDOSE3. First, S factors are calculated based on standard mathematical human phantoms. Actual patient anatomy in terms of organ shape and size as well as inter-organ position might be very different from any available phantom. Thus the S factors for any individual may vary considerably from the standard phantom.

Second, MIRDOSE3 assumes a uniform distribution of activity in the source organs. It has no way to incorporate non-uniform distribution of the source activity when the information becomes available.

Third, output from MIRDOSE gives only an average absorbed dose in the target organs. No spatially varying radiation dose or statistical information of the dose distribution within an organ (e.g., a volume-dose histogram) is available except for red marrow.

Fourth, the dose estimates for beta particles are calculated assuming complete local absorption. No consideration is given to the range of the beta particles; i.e., cross-fire between adjacent organs.

When the radionuclide is used for diagnostic purposes, normal tissue doses are well below tissue radiation tolerance. Therefore, MIRDOSE3 has sufficient accuracy for absorbed dose estimates in diagnostic imaging studies.

One conventional alternative method uses a "real-time" Monte Carlo calculation for radioimmunotherapy dosimetry. The advantage of a Monte Carlo approach is its flexibility and accuracy. Patient-specific information in terms of anatomy and tissue inhomogeneity can all be incorporated into a Monte Carlo simulation. However, a drawback of Monte Carlo is its extensive computational time. Monte Carlo calculations are by nature time-consuming, because a statistically acceptable answer requires numerous pseudo-particles to be generated and their histories followed.

Several methods to do patient-specific dose estimates have been proposed by different groups. One method proposes a "real-time" Monte Carlo calculation for radioimmunotherapy dosimetry (T. K. Johnson and R. L. Vessella, "On the Possibility of 'Real-Time' Monte Carlo Calculations for the Estimation of Absorbed Dose in Radioimmunotherapy," Compute. Meth. Progr. Biomed., Vol. 29, pp. 205–210 (1989) and T. K. Johnson and S. B. Colby, "Photon Contribution to Tumor Dose from Considerations of 1311 Radiolabeled Antibody Uptake in Liver, Spleen and Whole Body," Med. Phys., Vol. 20(6), pp. 1667–1674 (1993)).

The MABDOSE code (of T. K. Johnson et al.) currently executes in a "reasonable" amount of time on a CRAY Y-MP/832 supercomputer. For a general institution without large computational power, the Monte Carlo approach is probably not feasible currently. A second problem with a Monte Carlo simulation is that the surface of the organs described in Monte Carlo code is usually required to be in analytical form (e.g., sphere, cylinder, plane or a volume composed by those surfaces). In a clinical situation, patient's organs have an arbitrary geometric shape. Thus it is difficult to directly use the CT 3-D anatomy in any Monte Carlo calculation without using crude approximations.

Another conventional alternative approach uses a point source function (PSF). The PSF is conceptually simple and easy to implement yet it can give patient-specific dose estimates. One drawback of the PSF method is that it is very difficult to incorporate tissue inhomogeneity into consideration since the point source function can only be generated assuming an infinite, homogenous medium. The point source function is isotropic and solely a function of r, the distance from the point source to target point. Another difficulty is the choice of grid size. In PSF, the doses from source point to target are given as a function of the distance between them. The assumption is that the size of source and target cells are much smaller than the distance. For a radionuclide of interest in RIT, the beta range is usually fairly small (e.g., in the order of mm). Therefore, in order to use the PSF, a patient's CT slice must be subdivided into a small grid matrix so that each pixel is small enough and can be approximated as a point. There are several difficulties in doing this. First, the computation time increases geometrically with the number of points. Sgouros et al. reported an overnight calculation using PSF to estimate dose contours for only one organ (liver) (G. Sgouros, S. Chiu, K. S. Pentlow, et al. "Three-Dimensional Dosimetry for Radioimmunotherapy Treatment Planning," J. Nucl. Med. 34, 1595–1601 (1993)). Second, the nuclear image data acquired usually is much coarser than the calculation grid size. Thus it does not make very much sense to carry the dose calculation to such a fine scale. On the other hand, if the grid size is made too large, e.g., comparable to the size of nuclear medicine image pixels, the error caused by approximating each pixel as a point might be fairly large. This is particularly true when the range of beta emitted is smaller than or comparable to the size of nuclear image pixels. In such a case, the dose to each point is mainly contributed by the cell containing it and close neighboring cells.

As explained above, for radioimmunotherapy, where a beta emitter is used to deliver therapeutic doses to tumor sites, the accurate estimation of the radiation dose to therapy-limiting tissues is much more demanding in order to maximize the therapeutic benefit while minimizing unnecessary radiation exposure.

SUMMARY OF THE INVENTION

It is therefore an object of the present invention to provide a system and method that determines internal radioactivity and absorbed dose estimates of a patient more accurately and with greater ease.

It is a further object of the present invention to provide a system and method for determining internal radioactivity of a patient even with high background radioactivity and/or overlapping organs by using uptake information from the gamma camera images and anatomic data from CT scans.

It is another object of the present invention to provide a system and method for determining internal absorbed dose estimates of a patient by using the actual patient's anatomy in terms of organ shape and size as well as inter-organ position, without the use of phantom shapes, as in conventional absorbed dose estimation methods.

It is a further object of the present invention to provide a system and method for determining internal absorbed dose estimates of a patient without assuming a uniform distribution of activity in the source organs, so as to be able to incorporate non-uniform distribution of the source activity if the information is available.

It is a further object of the present invention to provide a system and method for determining internal absorbed dose estimates of a patient which provides not only an average absorbed dose in the target organs but also provides spatially varying radiation dose or statistical information of the dose distribution within an organ (e.g., a volume-dose histogram).

It is a further object of the present invention to provide a system and method for determining internal absorbed dose estimates of a patient in which the dose estimates for beta particles are calculated without assuming local absorption and in which consideration is given to the range of the beta particles; i.e., cross-fire between adjacent organs.

The foregoing and other objects, features and advantages of the invention will be apparent from the following more particular description of a preferred embodiment of the invention, as illustrated in the accompanying drawings wherein like reference numbers represent like parts of the invention.

DETAILED DESCRIPTION OF THE INVENTION

Figure 1:
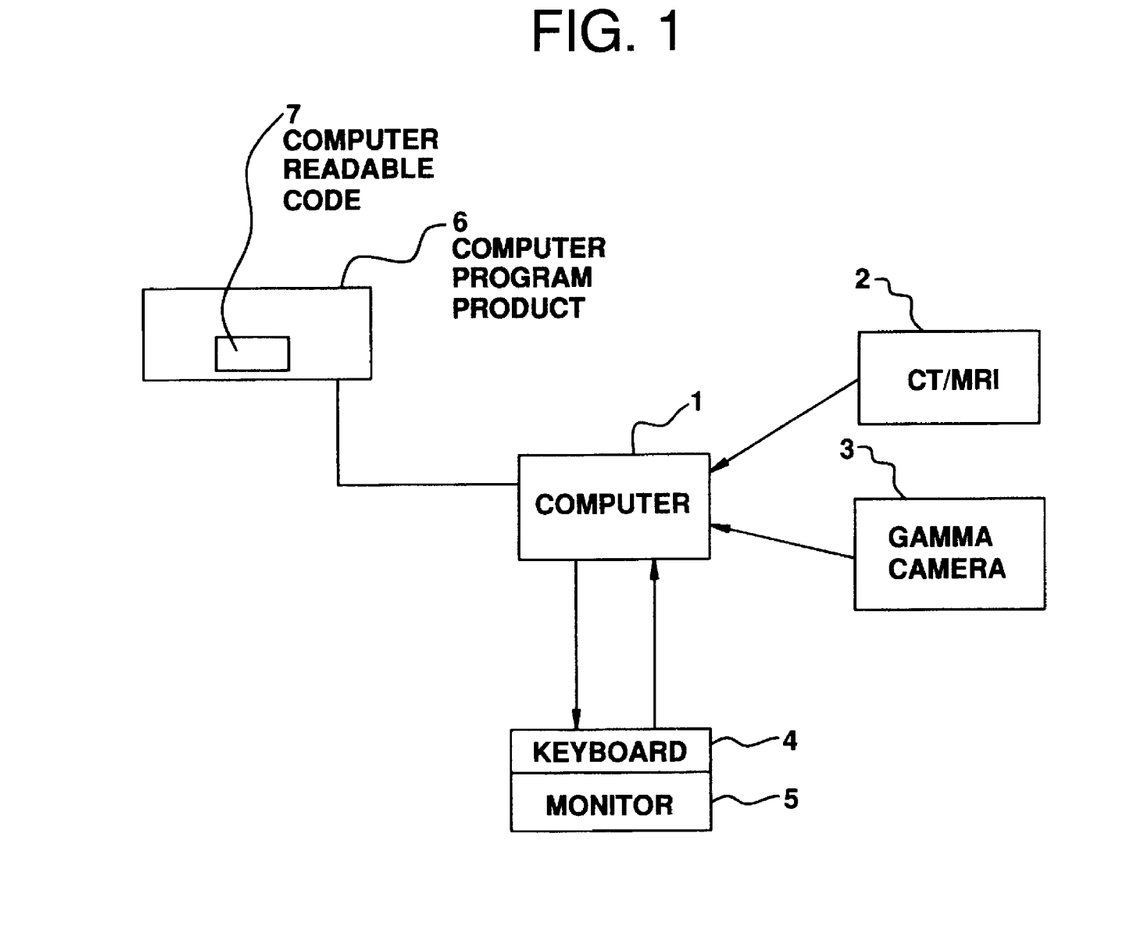
FIG. 1 is a block diagram of a preferred embodiment of the internal radiation and absorbed dose estimation system of the present invention.

The present invention may be implemented in a computer system 1 with a CT/MRI system 2 and a gamma camera 3, such as that shown in FIG. 1.

The computer system is preferably a SUN-Sparc 10 workstation, but any workstation, personal computer, minicomputer or mainframe computer may be employed. The computer system preferably has a processing unit, random access memory and permanent storage. Also, an optical communications adaptor may enable communication with other computer systems.

FIG. 1 provides an exemplary arrangement of components used in the preferred embodiment. Therefore, other components with similar function could replace those shown in FIG. 1.

The preferred embodiment is a computer implemented process operating on computer system 1. Images from CT/MRI 2 and Gamma Camera 3 are transmitted to computer 1 to be processed and viewed on monitor 5. A user may operate keyboard 4 as desired. Computer 1 then carries out the operations described below using a computer program product 6 having a computer readable code 7.

Figure 2:
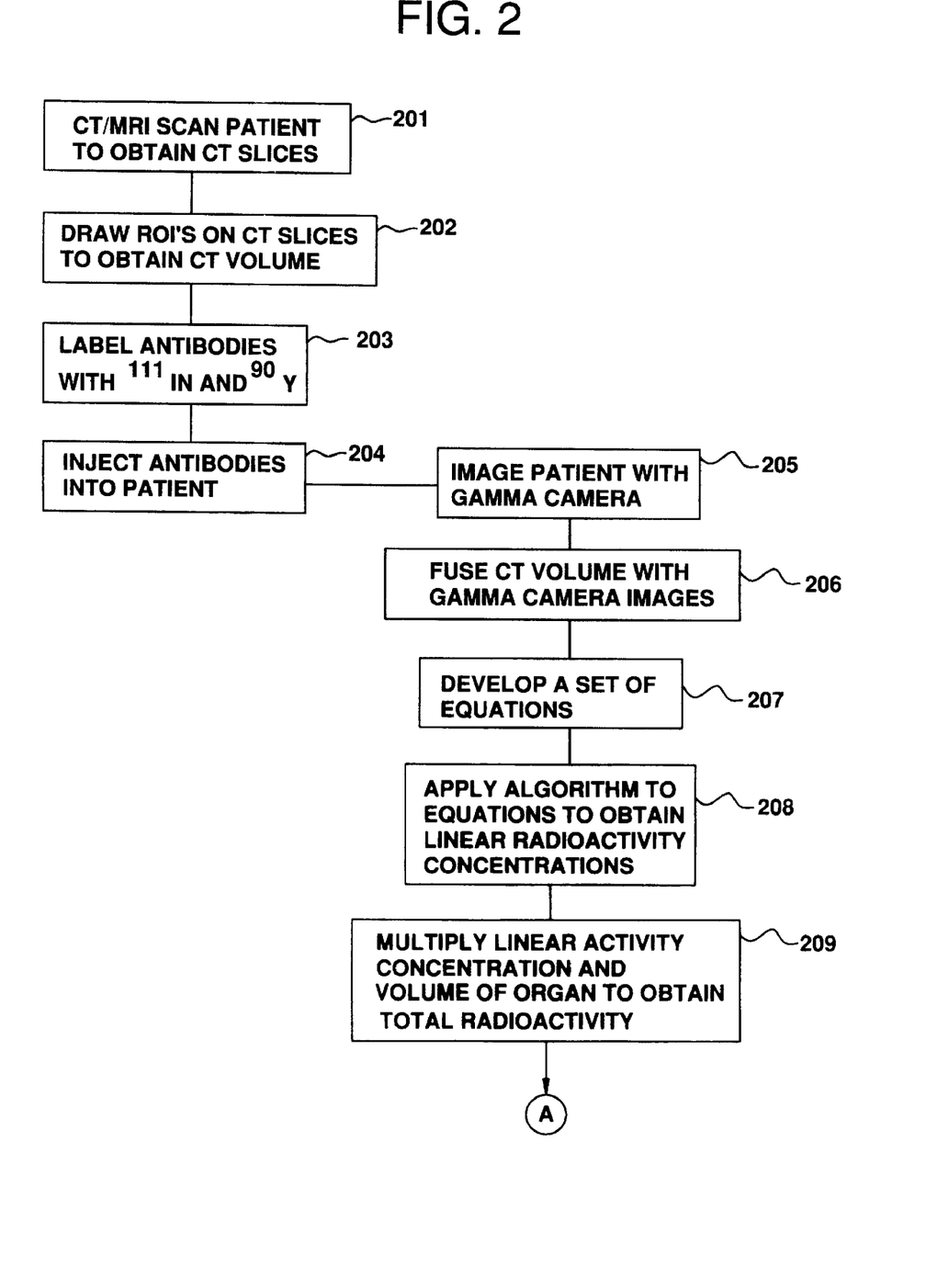
FIG. 2 is a flow chart depicting the steps employed in the present invention to determine the internal radioactivity of a patient.
Figure 3:
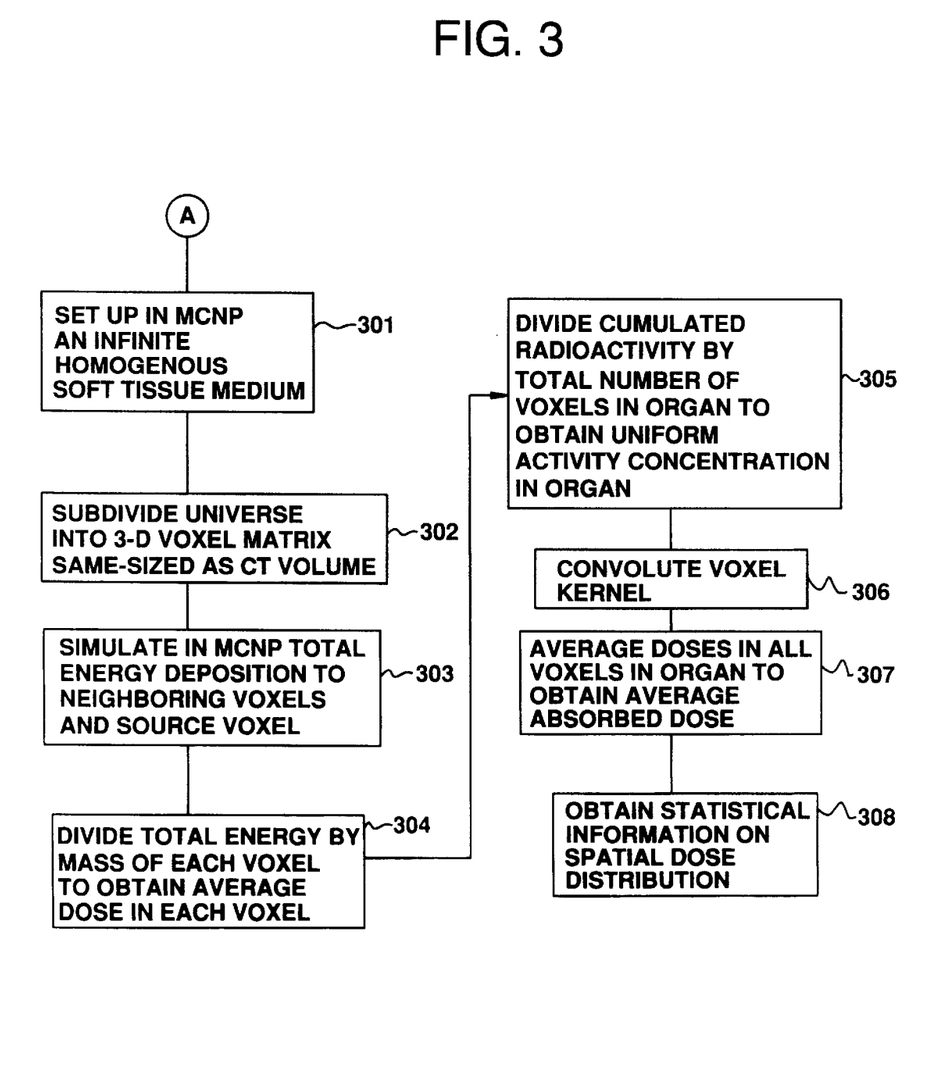
FIG. 3 shows a flow chart depicting the steps employed in estimating the average dose to an organ and in obtaining statistical information.

The present invention operates according to the steps shown in FIGS. 2 and 3. First, a patient is CT or MRI scanned to obtain CT slices over the relevant regions of the patient's body at 201. For example, a GE Hi-speed Advantage CT system (Milwaukee, Wis.) may be used to acquire CT images. For a patient's chest and abdominal series, a slice interval of 1.0 cm may be used.

Regions of interest are then drawn on the CT slices to obtain a CT volume at 202.

Next, antibodies are labelled with $^{111}$In and $^{90}$Y at 203, and the antibodies are injected into a patient at 204.

Then, an area of the patient is imaged with a gamma camera to obtain anterior and/or posterior gamma images at 205. For example, a Toshiba dual-head scintillation gamma camera (model GCA-7200A) fitted with medium energy parallel-hole collimator may be used to acquire nuclear medicine images. The gamma camera may be peaked for $^{111}$In (photon energies 173 Kev and 245 Kev) with a 20% symmetric window.

Next, the anatomical information from the CT volume and the radioactivity information from the gamma camera image are fused at 206. To do this, the CT volume is transformed into a two dimensional coronal projection and added to the two dimensional gamma camera image. That is, the CT volume is adjusted in size to have the same scale as the nuclear medicine planar images.

More specifically, the CT image is visually moved on a monitor until the organ boundaries on the CT image coincides with those on the gamma camera images. When the organ boundaries are not visible on nuclear medicine images, body contours from both the CT projection and nuclear medicine images could be used as a marker to help registration.

A user controls the fusion operation registering CT and gamma camera images. This is used instead of an autoregistration technique to avoid problems caused by large anatomical changes between CT and gamma camera scans.

That is, during the CT procedure, patients are asked to hold their breath, while patients are allowed to breath normally during the gamma camera scan. This causes the position of the patient's diaphragm to differ between the two images. Therefore, the registration cannot be a simple global translation and rotation operation since the relative inter-organ positions can change between the two imaging modalities.

A second reason for a user controlled fusion approach is that contrast on the gamma camera images is relatively poor so that auto-registration would not work very well, but on the other hand, the visual fusion technique is appropriate for this situation.

Next, to obtain a linear radioactivity density, a set of equations are developed by uniformly selecting several hundred points (N) from the gamma camera image at 207.

More specifically, for each image point (i) selected:

$$C_i = \left[ \int_0^T a_i(x) B_i(x) e^{-\mu x} dx \right] CF; \quad (4)$$

where $C_i$=cpm from gamma camera image at the calculation point;

$a_i(x)$=linear radioactivity density at depth of x along the point ($\mu$Ci/cm);

$B_i(x)$,$\mu$ and CF have been defined in equation (1b) above.

Notice that this result is a generalization of equation (1a).

Under the assumption that the radioactivity density, i.e., $a_i(x)$, in any organ is uniform, equation (4) can be simplified by taking the linear radioactivity density out of the integral. It may also be assumed that $B_i(x)$ does not vary appreciably over the range of integration so that it also may be replaced by an average buildup factor. Thus:

$$C_i = \left[ \sum_{j=1}^{n} \overline{a_j B_j} \frac{(e^{-\mu l_{1,j}} - e^{-\mu l_{2,j}})}{\mu} \right] CF \quad (5)$$

where n=the number of organs that can be seen under the calculation point, or in the general case, the number of organs for which we want to calculate the activity. n is on the order of 10 in clinical situations.

$a_j$=the average linear radioactivity density in the organ j($\mu$Ci/cm). This is the set of unknowns, 1<j<n.

$B_j$=the average buildup factor for the organ j taken as the buildup factor at the center position of the organ;

$l_{1j}$ and $l_{2j}$=the distances from the upper and lower boundary of the organ j to the body surface respectively (cm).

In equation (5), $l_{1j}$ and $l_{2j}$ can be obtained from the CT volume image. So $a_j$ are the only unknown variables (n unknowns). With N points (N>>n) selected, equations (5) form an overdetermined linear equations set.

$$[C]^{N \times 1} = [H]^{N \times n} [a]^{n \times 1} \quad (6)$$

where [H] is defined as the product of the known quantities in equation (5). Bold letters are used to represent matrices.

Equation (6) can be solved by a numerical matrix inversion which is equivalent to least square fit of the equation set:

$$[a]^{n \times 1} = [H^{-1}]^{n \times N} [C]^{N \times 1} \quad (7)$$

This numerical matrix inversion gives the average activity density for the organs as well as the associated statistical standard deviations for the variables estimated.

Then, to calculate total radioactivity in the organs of interest, the linear activity concentration is multiplied by the CT volume of each organ at 209.

In order to get the effective attenuation coefficient and buildup factor, a thin uniform circular source of diameter 4.89 cm containing 880 $\mu$Ci (32.56 MBq) of $^{111}$In may be used. The source is imaged in air and at multiple depths created by tissue-equivalent polystyrene slices, ranging from 1.0 cm to 28.0 cm. The source is made as uniform as possible so that there is a constant amount of radioactivity per unit area.

After the images are taken, the curve representing the buildup factor and calibration factor (CF) of the camera is calculated on a per-pixel basis, i.e., count rate (cpm) per pixel of the image versus radioactivity in each pixel is acquired to be used in the calculation procedures. Using program SAAM II, a buildup factor of the form:

$$B(x) = K_0 + K_1 x + K_2 x^2 + K_3 x^3 + K_4 x^4 \quad (8)$$

is fit to the data.

The cumulated activity within each organ can be integrated from time-activity data by simple trapezoidal interpolation. A 3-D volume of the patient is built from patient's CT slices. Each voxel in the CT volume may have dimensions of 0.4 cm×0.4 cm×1.0 cm.

Figure 8A:
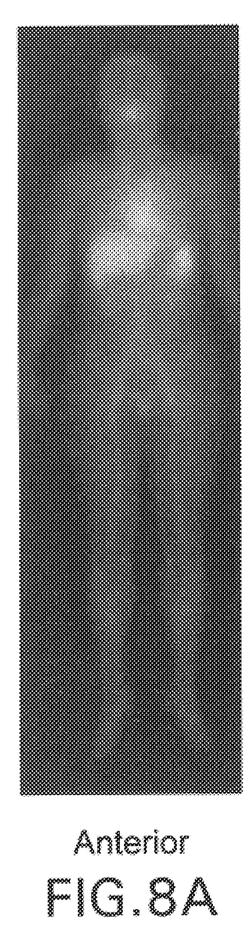
FIG. 8 shows whole body nuclear medicine images with regions of interest from the CT data set, from left to right, anterior image, posterior image, and anterior image with regions of interest from CT data.
Figure 8B:
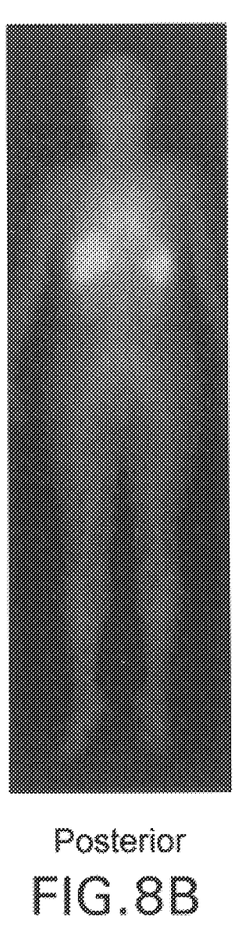
Figure 8C:
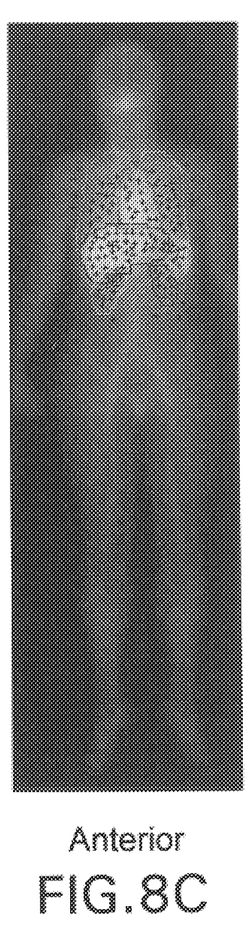

The present invention has been applied to a clinical study using the chimeric anti-CEA monoclonal antibody (cT84.66) with results given in Table 1. The patient (JC) was injected with 5 mCi $^{111}$In labeled Mab. Images shown in FIG. 8 were taken 2.38 hours after injection. For large organs with high activity contrast to background, e.g., liver, the difference between the Thomas' geometric mean method and the CAMI method was generally small. But for other organs with lower activity like kidneys and lungs, the difference could be as large as 50%. For those organs whose boundaries were not visible in the gamma camera images, conventional methods cannot be used to estimate activity. Organs with higher counts, e.g., liver, spleen and heart, usually have smaller standard deviation of the estimated activity due to better statistics. For later time points, the radioactivity left in the organs became less, so the standard deviation became larger.

It can be seen from Table 1 that the CAMI gave internally consistent results. Two parts of the same system, left kidney versus right kidney and left lung versus right lung, have very similar linear density. For example, the left kidney uptake (in FIA) at 2.38 hours was estimated as 0.0123±21.2% while the right kidney value was 0.0102±19.4%. In the corresponding lung comparisons, left lung estimated uptake was 0.0465±8.8% whereas right lung estimated uptake was 0.0530±8.5%. This indicated that the uptake of activity was tissue dependent.

places an exclusion zone around high activity sources prior to selection of the N point set.

Errors in the CAMI methodology arise from a variety of causes. From the statistical variances seen in the inversion process, it was demonstrated that such uncertainties were generally small compared to the absolute errors seen in the phantom estimates. Because of the scatter effect seen above, the primary experimental problem is probably elimination of scatter radiation from adjacent tissues and background. Since the outline of the organ(s) is simply acquired in the CT scan, exclusion of a scatter zone around a relatively concentrated source of activity should not be difficult. This problem was compounded here since Compton scatter of the higher energy peak of $^{111}$In caused scattered photons to appear within the lower-energy window of the gamma camera spectrometer. Thus, the situation may be simplified by use of a single photon radionuclide and/or an asymmetric energy window on the camera. Some reduction in count rate would ensue in such conditions.

In addition to scatter, there are approximation errors which occur, of necessity in the matrix inversion process. While it is difficult to be precise about their relative magnitude, the two primary contributions to this uncertainty are due to assumptions made in going from equation (4) to equation (5). There, it was assumed that the density a(x) and the buildup factor B(x) could both be taken out of the integral and replaced by mean values. The first of these assumptions follows directly from the lowest-order approxi-

TABLE 1

Comparison of Patient (JC) Organ Uptakes Using Thomas et al. and CAMI Method.
% error shown in the parenthesis was from matrix inversion calculation.

|  | time (hrs) | 2.38 | 17.73 | 41.8 | 91.72 |
|---|---|---|---|---|---|
| whole body | CAMI | 0.976(+/−10.7%) | 0.861(+/−9.7%) | 0.634(+/−13.2%) | 0.325(+/−17.4%) |
| (FIA[b]) | Thomas | 0.976 | 0.820 | 0.610 | 0.318 |
| liver | CAMI | 0.132(+/−2.4%) | 0.135(+/−2.0%) | 0.126(+/−2.1%) | 0.0829(+/−2.1%) |
| (FIA[b]) | Thomas | 0.177 | 0.177 | 0.157 | 0.101 |
| spleen | CAMI | 0.0399(+/−5.1%) | 0.0257(+/−6.6%) | 0.0129(+/−13.0%) | 0.0057(+/−19.3%) |
| (FIA[b]) | Thomas | 0.0391 | 0.0293 | 0.0171 | 0.00733 |
| l_kidney | CAMI | 0.0123(+/−21.2%) | 0.0117(+/−18.6%) | 0.00987(+/−21.7%) | 0.00250(+/−56.1%) |
| (FIA[b]) | Thomas | 0.00736 | 0.00815 | 0.00619 | 0.00244 |
| r_kidney | CAMI | 0.0102(+/−19.4%) | 0.00816(+/−20.5%) | 0.00627(+/−26.1%) | 0.00251(+/−42.6%) |
| (FIA[b]) | Thomas | —[a] | —[a] | —[a] | —[a] |
| heart | CAMI | 0.0731(+/−4.3%) | 0.0479(+/−5.4%) | 0.0289(+/−8.9%) | 0.0106(+/−15.8%) |
| (FIA[b]) | Thomas | 0.0836 | 0.0587 | 0.0397 | 0.0147 |
| l_lung | CAMI | 0.0465(+/−8.8%) | 0.0329(+/−10.2%) | 0.0198(+/−16.8%) | 0.0073(+/−30.2%) |
| (FIA[b]) | Thomas | —[a] | —[a] | —[a] | —[a] |
| r_lung | CAMI | 0.0530(+/−8.5%) | 0.0427(+/−8.8%) | 0.0254(+/−14.6%) | 0.0118(+/−20.7%) |
| (FIA[b]) | Thomas | —[a] | —[a] | —[a] | —[a] |

[a]Thomas' method does not work in these cases due to a lack of anterior and posterior images.
[b]Fraction of total injected activity.

The initial results were obtained using a grid of N points placed uniformly over the nuclear planar image to establish linear densities. No dependence upon N was observed if the number of points was between 50 and 840. Moreover, no improvement in accuracy occurred with the use of a bilateral instead of unilateral nuclear image data. However, background uptake was consistently overestimated via the CAMI methodology in this context of a uniform grid.

A separate experiment was carried out to determine if Compton scatter was enhancing the apparent uptake in the background volume. By positioning a linear (one-dimensional) grid of matrix inversion points at different distances from the edge of a phantom organ with relatively high uptake (spleen), the scatter effect could be reduced by over a factor of two by moving the computational volume some 5 cm or further from the organ edge.

Such edge regions in background activity density computations may be avoided by using a simple algorithm which mation to a(x); i.e., that a constant activity density may represent a given organ. In the second case, extracting B(x) from the integral is also a lowest-order Taylor's Series approximation to the actual buildup function. In this case, the B(x) function was expanded about its value at the midpoint of the organ. Future improvements to these simplifications to the analytic process could, therefore, involve better representations of these functions within the integral of equation (4).

Geometric data from CT or MRI scans can be used to determine radionuclide uptake in a phantom or patient. Such anatomic information allows planar nuclear images to be interpreted in terms of organ uptakes at depth. These uptakes, determined via the CAMI algorithm, may be in organs which overlap or are not visible due to low contrast in the nuclear projection data. Conjugate view images and auxiliary nuclear imaging are not required. Accuracy of the CAMI method appeared to be within 15% for the phantom organ uptakes independent of projection or number of points (N>50) selected in the matrix inversion process. An additional feature of the method is that the geometric data intrinsic to the patient are immediately available; thus, patient-specific absorbed radiation doses may be estimated without recourse to MIRD or other generic phantoms.

The present invention does not require two conjugate images to be acquired; a single projection is sufficient to determine the unknown linear activity densities. Additionally, the present invention does not require organs to be visible on the nuclear medicine images and, correspondingly, there is no need to draw ROI's on the nuclear images. The CAMI technique is different from the one proposed by Goris et al. where ROIs are still needed to be drawn on gamma camera images and two conjugate images are still required for geometric mean calculation (M. L. Goris, S. A. Knox, K. R. Nielsen, O. Bouillant, "Organ Modeling in the Quantitation of Planar Images for Distribution Studies," *Cancer* 73(3), 919–922 (1994)).

The internal radioactivity determined by the CAMI technique may then be used to determine absorbed dose estimates as shown in FIG. 3.

In order to get the voxel source kernel (VSK) for $^{90}$Y, an infinite, homogenous soft tissue medium was set up in MCNP at 301. A general-purpose Monte Carlo code, originally developed at Los Alamos National Lab, may be used. Also, the same chemical composition of the soft tissue used in original MIRD phantom for the S value calculation may be used.

Next, the universe is subdivided into a 3-dimensional voxel matrix whose dimensions are the same as the one in the patient's 3-D CT volume (e.g., 0.4 cm×0.4 cm×1.0 cm) at 302.

The source is uniformly distributed within the central voxel and beta particles are isotropically emitted. The energy of the beta particles is sampled from a $^{90}$Y energy spectrum. Table 2 shows the MAVSK for $^{90}$Y in soft tissue and Table 3 gives the analogous result in lung tissue. Only the data in the first octant is shown because of spatial symmetry. Notice that since the range of betas from $^{90}$Y is only 1.1 cm, dose contribution from the source voxel to distant voxels is approximately zero assuming Bremsstrahlung radiation can be neglected.

Next, assuming unit activity uniformly distributed in the center voxel (position 0,0,0), the total energy deposition to the neighboring voxels as well as the source voxel are simulated in MCNP at 303.

Then, average doses in each voxel are calculated by dividing the energy deposited by the mass of each voxel at 304 and a look-up table is generated (Table 3).

The voxel source kernel for $^{90}$Y in lung tissue ($\rho=0.3$ gm/cm$^3$) is also calculated (Table 3) in a similar manner. In the simulation for the lung voxel source kernel, the chemical composition of lung tissue obtained from any technical reference or source may be used.

Next, a uniform activity concentration in each organ is obtained by dividing cumulated activity by the total number of voxels in that organ at 305. Then, the average absorbed dose to each voxel in the 3-D patient's CT volume is estimated by convoluting the

TABLE 2

Voxel Source Kernel (MAVSK) for $^{90}$Y in an infinite, homogeneous soft tissue medium ($\rho$ = 1.0 gm/cm$^3$). Voxel size is 0.4 cm × 0.4 cm × 1.0 cm (X,Y,Z direction respectively). The indices are the coordinates of the voxels. Because of symmetry[a], only the first octant is shown. The dose contribution from voxels outside the volume shown were approximated as zero in dose estimation. Values shown are in the units of mGy/disintegration.

| | X | | 0 | 1 | 2 | 3 | 4 | 5 |
|---|---|---|---|---|---|---|---|---|
| | Z | Y | | | ← Voxel Index → | | | |
| V | 0 | 0 | 3.9021E−07 | 7.1273E−08 | 3.1706E−09 | 1.9678E−11 | 9.6579E−13 | 5.5274E−13 |
| O | | 1 | 7.1247E−08 | 2.2792E−08 | 1.3298E−09 | 7.8382E−12 | 9.1375E−13 | 5.0823E−13 |
| X | | 2 | 3.1733E−09 | 1.3184E−09 | 7.8875E−11 | 1.3995E−12 | 7.3543E−13 | 4.8472E−13 |
| E | | 3 | 1.8963E−11 | 7.4764E−12 | 1.3642E−12 | 7.9975E−13 | 5.6046E−13 | 4.0635E−13 |
| L | | 4 | 8.9536E−13 | 8.2269E−13 | 7.5865E−13 | 6.0240E−13 | 4.5575E−13 | 3.0786E−13 |
| | | 5 | 5.6870E−13 | 5.2933E−13 | 5.1106E−13 | 3.6120E−13 | 2.9148E−13 | 2.3461E−13[b] |
| I | 1 | 0 | 2.2557E−08 | 6.9656E−09 | 3.9074E−10 | 3.0842E−12 | 6.6453E−13 | 4.4854E−13[b] |
| N | | 1 | 6.9560E−09 | 2.6199E−09 | 1.5981E−10 | 1.6192E−12 | 6.8070E−13 | 4.2479E−13[b] |
| D | | 2 | 3.9552E−10 | 1.6112E−10 | 1.0277E−11 | 8.5039E−13 | 5.2462E−13 | 4.4436E−13[b] |
| E | | 3 | 3.0406E−12 | 1.7516E−12 | 8.5597E−13 | 6.2810E−13 | 4.6827E−13 | 3.0570E−13[b] |
| X | | 4 | 7.3024E−13 | 6.5382E−13 | 5.6292E−13 | 4.0171E−13 | 4.0468E−13[b] | 2.6599E−13[b] |
| | | 5 | 4.0951E−13 | 4.2411E−13[b] | 3.9120E−13[b] | 3.3806E−13[b] | 3.0840E−13[b] | 2.2496E−13[b] |
| | 2 | 0 | 7.7510E−13 | 6.8870E−13 | 4.9825E−13 | 4.1083E−13 | 3.2817E−13 | 2.6948E−13[b] |
| | | 1 | 6.7711E−13 | 6.3140E−13 | 5.8263E−13 | 4.4292E−13 | 3.3731E−13[b] | 2.8321E−13[b] |
| | | 2 | 5.5699E−13 | 5.4900E−13 | 4.8784E−13 | 4.0140E−13 | 3.0283E−13[b] | 2.2356E−13[b] |
| | | 3 | 4.2493E−13 | 3.9633E−13 | 4.2614E−13[b] | 3.4755E−13[b] | 2.5749E−13[b] | 2.4099E−13[b] |
| | | 4 | 3.1679E−13 | 2.8393E−13[b] | 3.0111E−13[b] | 2.8881E−13[b] | 2.1715E−13[b] | 2.0006E−13[b] |
| | | 5 | 2.2410E−13[b] | 2.8249E−13[b] | 2.6185E−13[b] | 2.5117E−13[b] | 2.0570E−13[b] | 1.5884E−13[b] |

[a]Symmetry rule: VSK(X,Y,Z) = VSK(X,Y,-Z) = VSK(X,-Y,Z) = VSK(X,-Y,-Z) = VSK(-X,Y,Z) = VSK(-X,Y,-Z) = VSK(-X,-Y,Z) = VSK(-X,-Y,-Z)
[b]The statistics of these values were poor because of lack of sampling events. They were treated as zero in dose calculation.

TABLE 3

Voxel Source Kernel (MAVSK) for $^{90}$Y in an infinite, homogeneous lung tissue medium ($\rho$ = 0.3 gm/cm$^3$). Voxel size is 0.4 cm × 0.4 cm × 1.0 cm (X,Y,Z direction respectively). The indices are the coordinates of the voxels. Because of symmetry[a], only the first octant is shown. The dose contribution from voxels outside the volume shown were approximated as zero in dose estimation. Values shown are in the units of mGy/disintegration.

| | X | 0 | 1 | 2 | 3 | 4 | 5 |
|---|---|---|---|---|---|---|---|
| Z | Y | | | ← Voxel Index → | | | |
| V   0 | 0 | 4.4493E−07 | 1.1777E−07 | 2.9038E−08 | 1.0816E−08 | 4.2824E−09 | 1.5572E−09 |
| O     | 1 | 1.1696E−07 | 6.1147E−08 | 2.2694E−08 | 9.2702E−09 | 3.8495E−09 | 1.4121E−09 |
| X     | 2 | 2.8762E−08 | 2.2629E−08 | 1.2571E−08 | 6.2258E−09 | 2.6928E−09 | 1.0651E−09 |
| E     | 3 | 1.0675E−08 | 9.2661E−09 | 6.0689E−09 | 3.3897E−09 | 1.5703E−09 | 6.0111E−10 |
| L     | 4 | 4.1811E−09 | 3.8018E−09 | 2.6396E−09 | 1.5353E−09 | 7.3039E−10 | 2.4079E−10 |
|       | 5 | 1.5494E−09 | 1.3809E−09 | 9.8110E−10 | 5.7697E−10 | 2.4756E−10 | 8.5142E−11 |
| I   1 | 0 | 4.6279E−08 | 2.6831E−08 | 1.1997E−08 | 5.5393E−09 | 2.3762E−09 | 9.1529E−10 |
| N     | 1 | 2.6527E−08 | 1.9023E−08 | 1.0008E−08 | 4.9040E−09 | 2.1765E−09 | 7.8780E−10 |
| D     | 2 | 1.2024E−08 | 1.0013E−08 | 6.3012E−09 | 3.3755E−09 | 1.5141E−09 | 5.6955E−10 |
| E     | 3 | 5.3898E−09 | 4.7958E−09 | 3.2164E−09 | 1.8540E−09 | 8.2228E−10 | 3.2704E−10 |
| X     | 4 | 2.3456E−09 | 2.1245E−09 | 1.4776E−09 | 8.6871E−10 | 4.0268E−10 | 1.3893E−10 |
|       | 5 | 9.1644E−10 | 8.0910E−10 | 5.6534E−10 | 2.9658E−10 | 1.4577E−10 | 4.8237E−11 |
|     2 | 0 | 2.5336E−09 | 2.2572E−09 | 1.5960E−09 | 9.1556E−10 | 4.2366E−10 | 1.4202E−10 |
|       | 1 | 2.2702E−09 | 2.0097E−09 | 1.3595E−09 | 8.1993E−10 | 3.8682E−10 | 1.4955E−10 |
|       | 2 | 1.5715E−09 | 1.4542E−09 | 1.0208E−09 | 5.8315E−10 | 2.6200E−10 | 9.2800E−11 |
|       | 3 | 8.7763E−10 | 7.8392E−10 | 5.9343E−10 | 3.2260E−10 | 1.4085E−10 | 4.9761E−11 |
|       | 4 | 3.9900E−10 | 3.5000E−10 | 2.6783E−10 | 1.5302E−10 | 6.0515E−11 | 1.5012E−11 |
|       | 5 | 1.3853E−10 | 1.2116E−10 | 7.9950E−11 | 4.2811E−11 | 1.7480E−11 | 6.2576E−12 |

[a]Symmetry rule: VSK(X,Y,Z) = VSK(X,Y,−Z) = VSK(X,−Y,Z) = VSK(X,−Y,−Z) = VSK(−X,Y,Z) = VSK(−X,Y,−Z) = VSK(−X,−Y,Z) = VSK(−X,−Y,−Z)

MAVSK (kernel) with the 3-D activity distribution obtained from CAMI at 306.

Then the average absorbed dose in each organ is calculated by averaging the doses in all the voxels within the organ at 307. Statistical information such as standard deviation of the average dose in each organ as well as the dose-volume histogram is also obtained at 308.

Although uniform activity distribution within each organ is assumed in the above example, a non-uniform distribution of radioactivity could be easily incorporated into the present invention by using a radioactivity concentration look-up table at step 306.

Furthermore, if the tumors are visible in a patient's CT scan, tumor volumes can be obtained by drawing a boundary around the lesion. Thus, absorbed dose to tumor can also be estimated by the present MAVSK system and method.

The present invention was tested by simulating the point source function for $^{90}$Y and comparing the result with several published PSFs. In this example, MCNP was set up in such a way that the electron spectrum of $^{90}$Y is emitted isotopically from a point source in an infinitely homogeneous H$_2$O medium. Electrons and secondary photons are followed.

Figure 4:
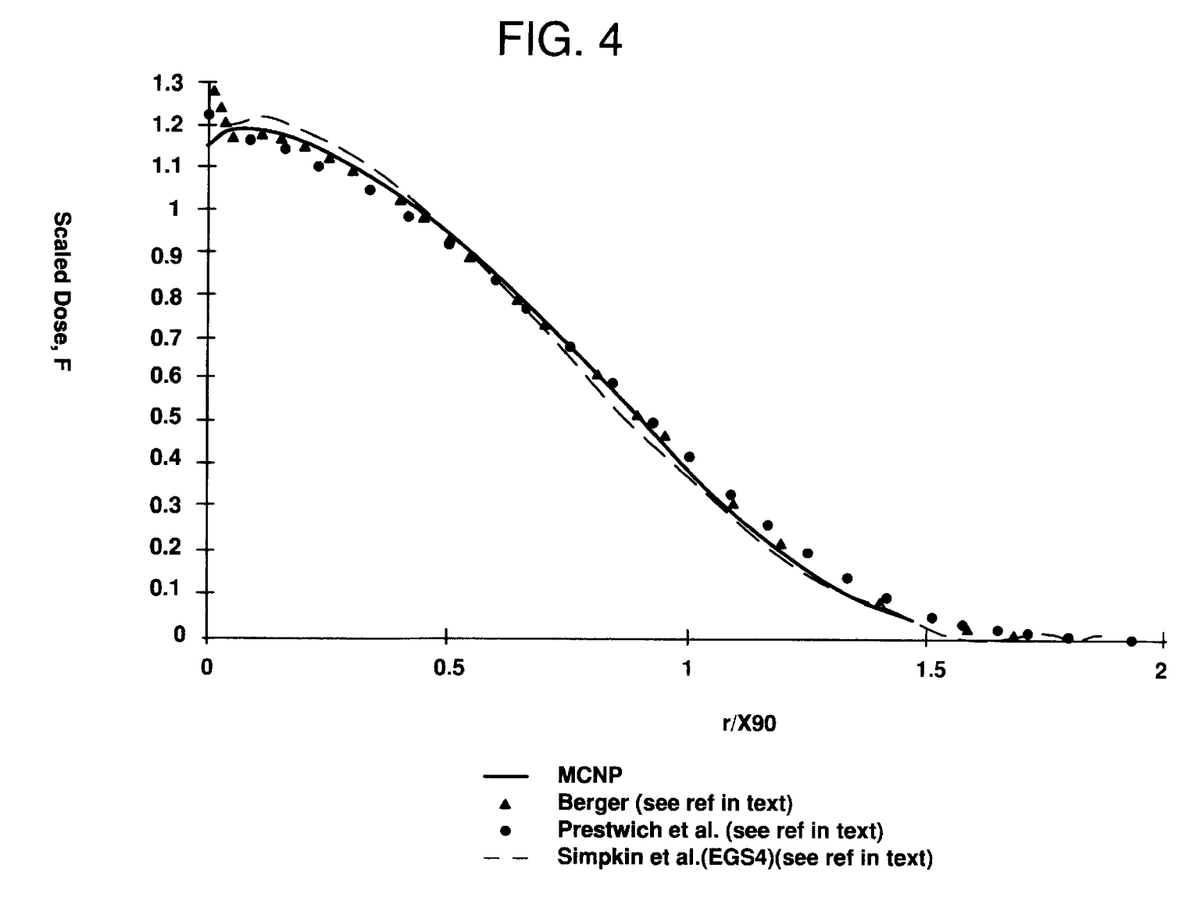
FIG. 4 shows a MCNP simulated scale point source dose kernel, $F(r/X_{90})$, for $^{90}Y$ beta decay, with results of other references shown for comparison.

Energy deposited along each electron step is scored in spherical shells of thickness 25 $\mu$m. Electrons and photons are transported down to 10 Kev, below which their energy is deposited on-site and the history terminated. This energy cutoff is chosen since the CSDA (continuous slowing down approximation) range of such electrons in H$_2$O is exceedingly short (2.5 $\mu$m). Two million electron histories are followed, from which the mean energy imparted to each shell and the associated standard deviation are determined. Results are shown in FIG. 4.

The results are shown in the form of scaled absorbed dose versus percentile distance which are defined by Berger. Standard deviations for the MCNP results are all smaller than 1.0% and are not displayed. Data included are from Berger et al., Prestwich et al. and Simpkin et al. (M. J. Berger, "Distribution of Absorbed Dose Around Point Sources of Electrons and Beta Particles in Water and Other Media," MIRD Pamphlet No. 7, *J. Nucl. Med.*, Volume 12: Suppl. No. 5, pp. 5–24 (1971); W. V. Prestwich, J. Nunes, and C. S. Kwok, "Beta Dose Point Kernels for Radionuclides of Potential Use in Radioimmunotherapy," *J. Nucl. Med.*, Volume 30, pp. 1036–1046 (1989); D. J. Simpkin, T. R. Mackie, "EGS4 Monte Carlo Determination of the Beta Dose Kernel in Water," *Med. Phys.*, Volume 17(2), pp. 179–186 (1990)). The simulated results (solid line) from MCNP are in very good agreement with experimental data as well as with other Monte Carlo simulations (e.g., EGS4) with differences at all distances generally within 2%.

A patient study was performed using patient activity data calculated by the CAMI method. The area under the curve (AUC) yielded residence times (in MBqHour) for each organ which could be inserted into the MIRDOSE3 program to obtain dose estimates. All AUCs used in this embodiment are calculated by simple trapezoidal integration. Integration after the last time point is carried out by assuming purely physical decay of the isotope, which is probably an overestimate of the residence time.

Absorbed dose estimates based on AUC data determined above are shown in Table 4. For comparison,

TABLE 4

MAVSK and MIRDOSE3 comparison on patient data. The value shown are in the units of mGy/MBq. In MIRDOSE3 output, the left kidney and right kidney are treated as a single organ. Only one dose estimate can be given; a similar result holds for the lungs.

| organs | Patient #1 MAVSK(STDa) | MIRDOSE3 | Patient #2 MAVSK(STDa) | MIRDOSE3 |
|---|---|---|---|---|
| Liver | 13.49(1.12) | 13.4 | 9.27(0.68) | 25.0 |
| Spleen | 9.45(1.05) | 14.0 | 3.31(0.33) | 9.11 |
| Left Kidney | 7.85(0.86) | 6.98 | 6.33(0.73) | 8.42 |
| Right Kidney | 3.80(0.44) |  | 6.41(0.69) |  |
| Heart | 6.70(0.60) | 5.18 | 1.66(0.17) | 1.80 |
| Left Lung | 3.23(0.35) | 8.28 | 0.411(0.15) | 0.951 |
| Right Lung | 4.05(0.45) |  | 0.493(0.48) |  |
| Residual Body | 0.465(0.45) | 0.819 | 0.235(0.32) | 0.856 |

$$^a\text{Standard Deviation} = \sqrt{\frac{\sum_{i=1}^{N} \cdot (\overline{\text{Dose}} - \text{Dose}_i)^2}{(N-1)}},$$

where N is the total number of voxels in the organ and Dosei is the dose in voxel i. No statistic variables are available in MIRDOSE3.

results using the MIRDOSE3 program are also shown. Patient #1 was a normal size female (weight of 114 lbs, height of 5'1), similar to the female phantom described in MIRDOSE3 (nominal weight=125 lbs). Difference between MAVSK and MIRD results were not very marked. Patient #2 was a large size female (weight of 186 lbs, height of 5'6") with some large size organs (e.g., liver and spleen). As can be seen, the differences between MAVSK and MIRDOSE3 estimates could be as large as a factor of three in this case.

A simple modification to MIRDOSE3, suggested by Mike Stabin at Oak Ridge National Lab, is to adjust the MIRDOSE3 results by the patient's organ masses when those organs are very different from standard MIRD sizes. Adjusted MIRDOSE results can be calculated by the following formula;

$$\text{Adjusted } \textit{MIRDOSE} = (\textit{MIRDOSE Output}) \times \frac{\textit{MIRD} \text{ Organ Mass}}{\text{Patient Organ Mass}} \quad (9)$$

The results are shown in Table 5. For liver, spleen, kidneys and heart, the radioactivity concentration are higher than neighboring organs and tissue background. The dose contribution are mainly due to the radioactivity inside themselves. Adjusted MIRDOSE results become fairly close to the ones estimated by MAVSK with difference smaller than 15%. However, for lungs, a relatively large portion of dose comes from neighboring organs. The difference is still significant between MIRDOSE3 and MAVSK with errors of about 40%. This occurred because MIRDOSE3 neglects dose contributions from other organs for beta particle irradiations.

TABLE 5

MAVSK and Adjusted MIRDOSE3 comparison on patient #2 data. In MIRD output, the left kidney and right kidney are treated as a single organ. Only one dose estimate can be given; a similar result holds for the lungs.

|  | Organ Masses (gm) |  | Dose (mGy/MBq*Hour) |  |  |
|---|---|---|---|---|---|
| organs | MAVSK | MIRDOSE3 | MAVSK | Adjusted MIRDOSE3a | % Difference |
| Liver | 3549 | 1400 | 9.27 | 9.86 | 6.4 |
| Spleen | 374 | 150 | 3.31 | 3.65 | 10.4 |
| Left Kidney | 163 | 275 | 6.33 | 7.19 | -3.6 |
| Right Kidney | 159 |  | 6.41 |  |  |
| Heart | 799 | 650 | 1.66 | 1.46 | -11.8 |
| Left Lung | 593 | 651 | 0.411 | 0.51 | -40.2 |
| Right Lung | 632 |  | 0.493 |  |  | aAdjusted by patient's actual organ mass. See Eq. (9).

Figure 5:
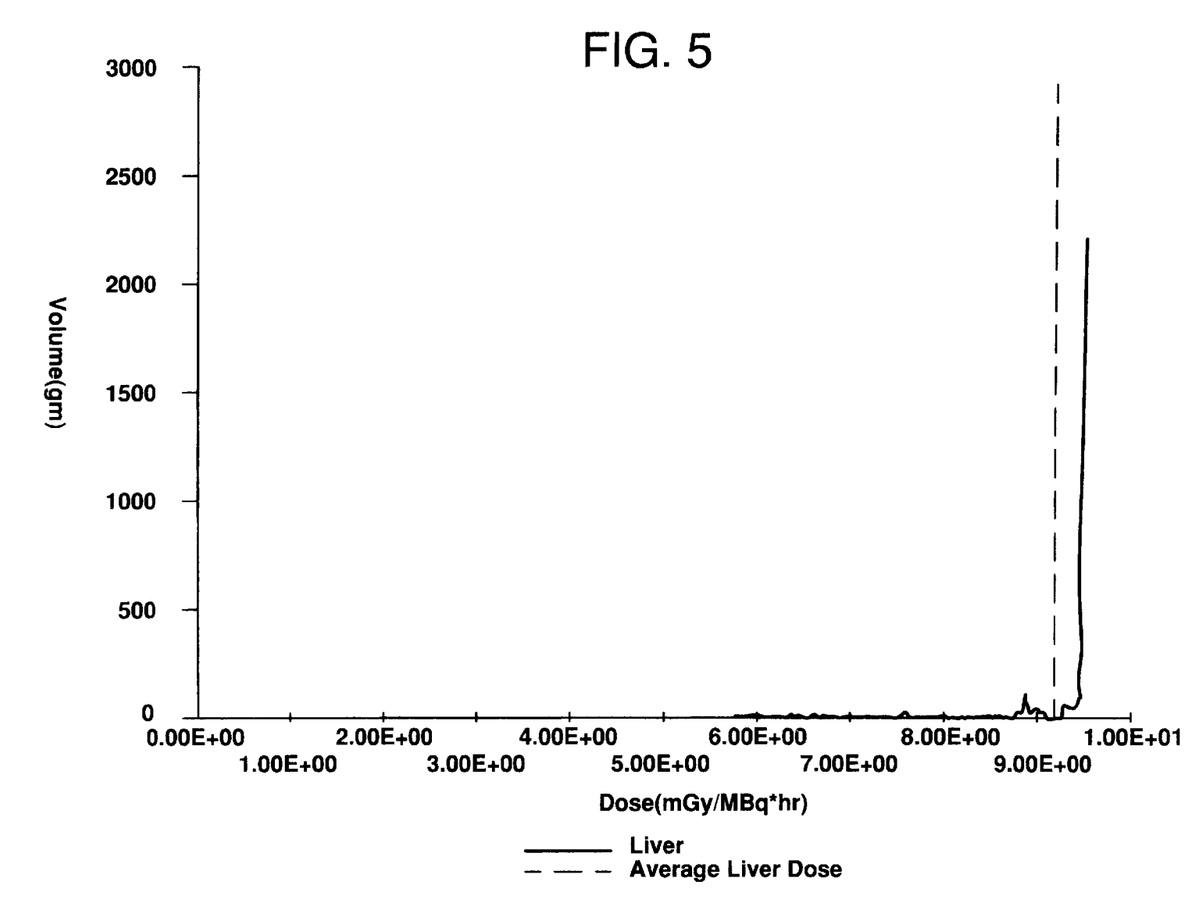
FIG. 5 shows a volume-dose histogram for liver in a patient.
Figure 6:
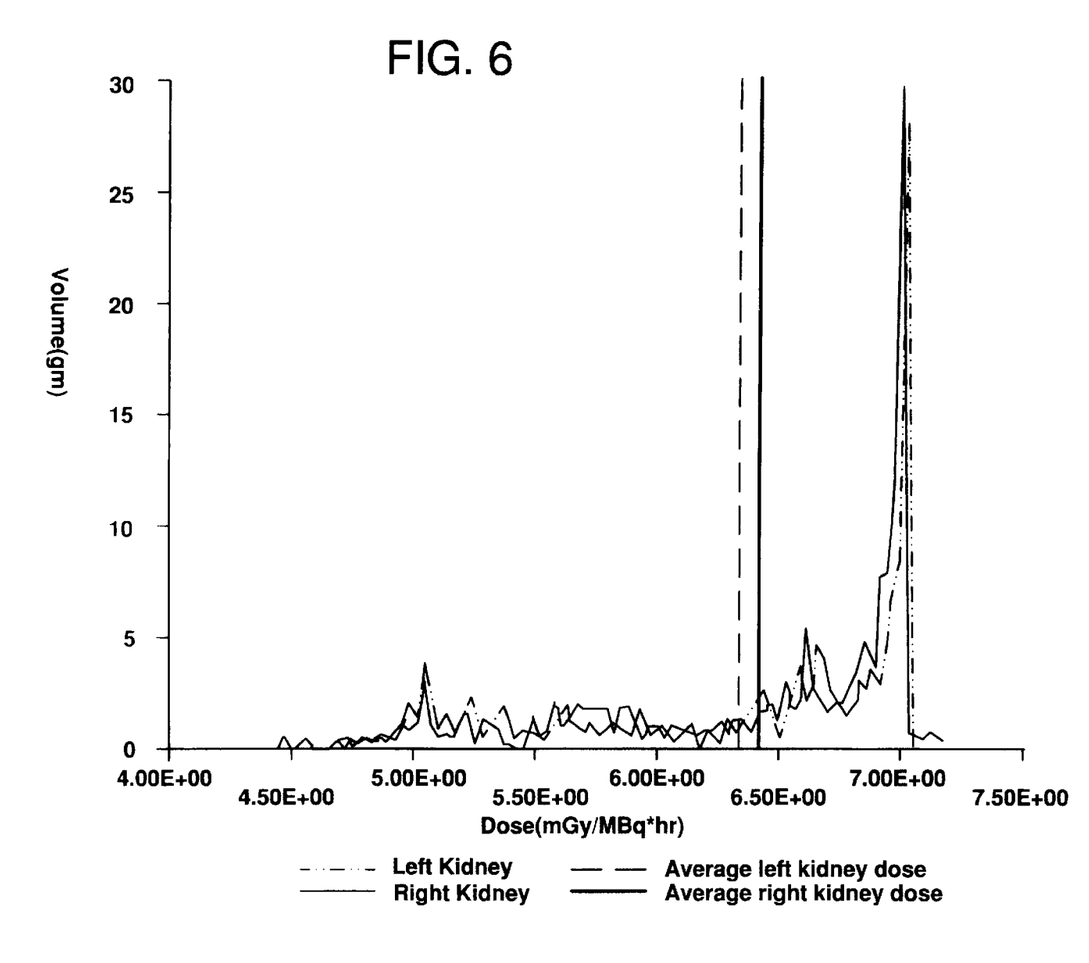
FIG. 6 shows a volume-dose histogram for kidneys in a patient.
Figure 7:
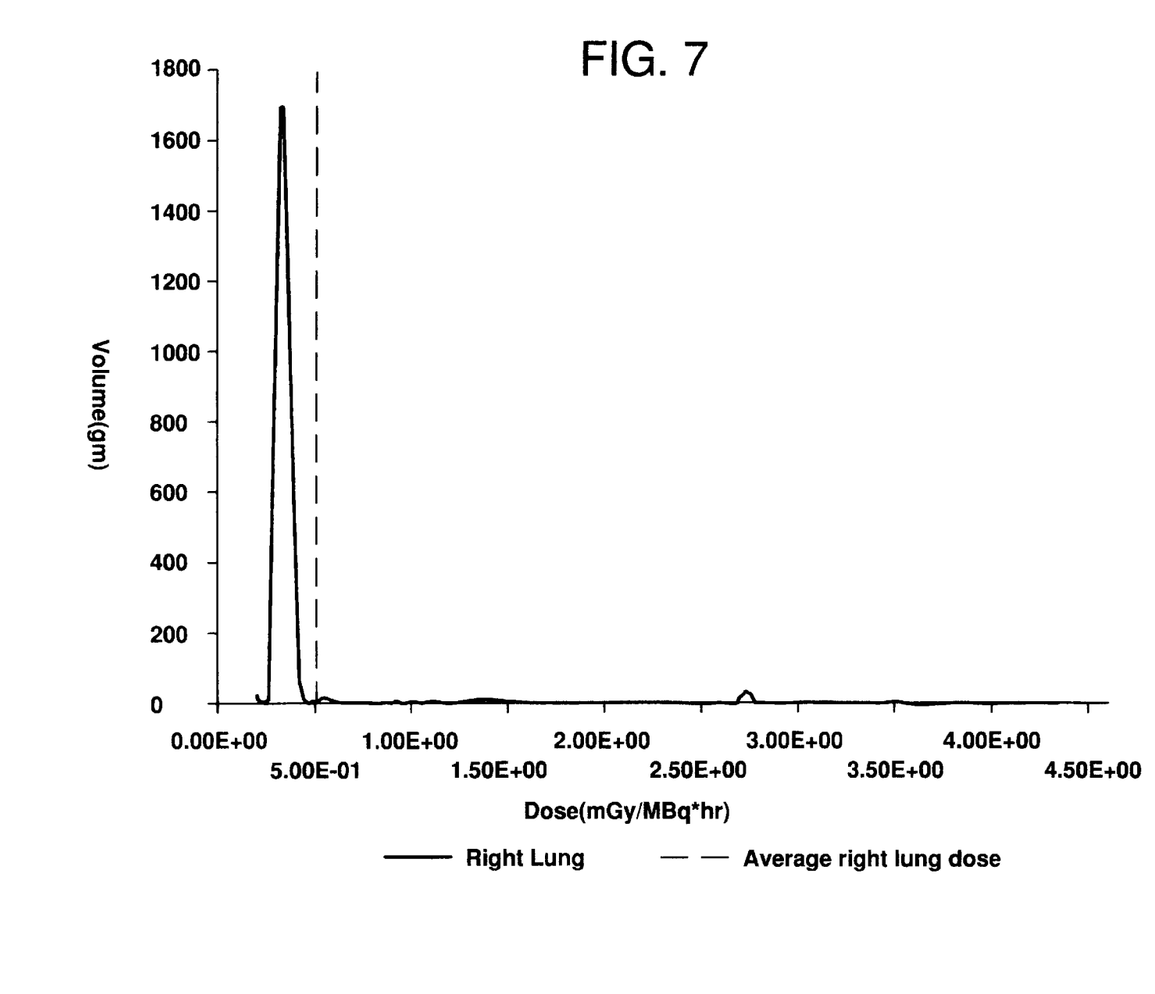
FIG. 7 shows a volume-dose histogram for a right lung in a patient.

An advantage of the MAVSK method over the current MIRDOSE3 program is that it gives statistical information of the absorbed dose distribution. FIGS. 5–7 show the volume-dose histogram (VDH) for patient #2. The present MIRDOSE3 algorithm only gives such information for red marrow absorbed dose. For all the other organs, MIRDOSE3 assumes a Dirac delta function for the VDH; i.e., every voxel in the organ receives a single dose. FIG. 5 shows VDH for the liver. Since the dose to liver voxels mainly came from the activity in liver itself, it was very similar to a delta function distribution. FIG. 6 shows the VDH for both kidneys. As can be seen, the cross-organ dose to kidneys from liver and spleen clearly made VDH farther away from a delta function. Since the right kidney was closer to the liver, some portion of right kidney received higher dose than average. This effect became more marked in the lung case (FIG. 7). Some portions of the right lung (voxels near the liver) had a radiation dose 10 times higher than average absorbed dose. Since the lungs is one of the major dose-limiting organs in RIT, this effect becomes essential during RIT treatment planning. Even if average lung dose is much below the lung dose threshold, some portions of the lungs still get much higher dose which later can become a carcinogenic factor.

A second advantage of the MAVSK method over Monte Carlo Calculation and other point source function methods is its real-time dose estimation capability. The Monte Carlo simulation of the VSK is a separate general calculation which can be run for relatively long periods to get good statistics on the voxel kernels. With a 4 day MCNP run on a SUN-Sparc 10 (Model 51) workstation, standard deviations obtained were less than 2% for all the voxels of interest. After the VSKs were acquired, the patient dose calculation was just the convolution of the VSKs over patient CT volume. This process took less than 1 minute per patient. Thus, patient-specific real-time dose estimates can be accomplished.

For beta radiation, an additional simplifying assumption made in the MIRDOSE3 program is that the beta radiation originating in the source organ is wholly absorbed in that organ without cross irradiation of adjacent tissue. For small or close-neighboring organs and high energy beta particle emitters, this assumption also needs to be improved. This limitation also occurs in its tumor dose estimation method. In the latest release of MIRDOSE3, the algorithm only considers absorbed dose contributed by activity located in the tumor itself. Dose contributions from surrounding organs or even the tumor-bearing organ are not considered. For example, absorbed dose to tumor from liver in the case of hepatic metastases or hepatoma. Similar improvements are also needed in the red marrow absorbed dose estimation to account for radioactivity in adjacent source regions, skeletal structures, and circulating blood. Thus it is clear that the current MIRDOSE system, while not necessarily wrong, needs to be modified so that it can be more flexible and can do better absorbed dose estimation for RIT.

In sum, the above described system and method determines internal radioactivity and absorbed dose estimates with more ease and accuracy than conventional systems.

The CAMI method permits uptake estimation in the common case where two or more organs overlap in the nuclear planar image; e.g., liver and right kidney in a planar projection. It is also applicable in cases where a planar image is simply not obtainable due to a lack of image contrast.

By alignment of nuclear planar and CT images, a simple matrix inversion process determines, via least squares, most likely values for the linear density of activity in the organ(s) of interest. These activity densities were then integrated over the organ volume to determine the total uptake in each tissue.

The Monte Carlo assisted voxel source kernel (MAVSK) system and method provides a novel way to perform real-time patient-specific absorbed doses for beta radionuclides. MAVSK does not require any extra nuclear scans for the patient and is easy to implement. Patient-specific organ doses as well as the dose volume histogram, and even 3-D isodose contours can all be calculated within 1 minute on a SUN-Sparc 10 workstation. Furthermore, a non-uniform distribution of radioactivity can be easily incorporated into MAVSK. Finally, tumor doses can also be estimated if desired; these doses could include contributions from adjacent organs.

The invention having been thus described, it will be apparent to those skilled in the art that the same may be varied in many ways without departing from the spirit and scope of the invention. Any and all such modifications are intended to be included within the scope of the following claims.

What is claimed is:

1. A method of determining radioactivity uptake of a patient, comprising the steps of:
    a) imaging a patient to obtain a first plurality of tomographic images;
    b) circumscribing at least one region of interest on at least one of said first plurality of tomographic images to obtain an image volume;
    c) imaging said patient to obtain at least one planar image corresponding to a radioactivity distribution field within said patient;
    d) fusing said image volume with said at least one planar image;
    e) obtaining a plurality of linear radioactivity densities each corresponding to an image point on said at least one planar image within said image volume; and
    f) multiplying said plurality of linear radioactivity densities by said image volume to obtain total radioactivity of said image volume.

2. A method of determining absorbed dose estimates of a patient using the method of claim 1, further comprising the steps of:
    a) simulating in a computer an infinite homogeneous soft tissue medium having a predetermined mass density;
    b) subdividing a predetermined area of said tissue medium into a 3-dimensional voxel matrix, wherein the dimensions of said voxel matrix are the same as the dimensions of said image volume;
    c) simulating a total energy deposition of a uniform unit of radiation energy from a source voxel to a plurality of neighboring voxels within said voxel matrix to determine an amount of energy deposited in each of said neighboring voxels;
    d) obtaining an average dose in each of said neighboring voxels by dividing said energy deposited in each of said neighboring voxels by a corresponding mass of each one of said plurality of voxels;
    e) dividing said total radioactivity of said image volume by a total number of voxels in said image volume to obtain a uniform activity concentration for each voxel of said image volume;
    f) calculating a voxel source kernel for said simulated homogeneous tissue medium;
    g) averaging doses of each one of said voxels in image volume to obtain an average absorbed dose of said image volume; and
    h) convoluting said voxel kernel with said image volume to obtain a dose for said image volume.

3. A method of determining absorbed dose estimates of a patient using the method of claim 2, further comprising the step of generating statistical information as to spatial dose distribution of said image volume by using at least said average absorbed dose.

4. An apparatus for determining internal radioactivity and/or absorbed dose estimates, comprising:
    a) means for imaging a patient to obtain a first plurality of tomographic images;
    b) means for circumscribing at least one region of interest on at least one of said first plurality of tomographic images to obtain an image volume;
    c) means for imaging said patient to obtain at least one planar image corresponding to a radioactivity distribution field within said patient;
    d) means for fusing said image volume with said at least one planar image;

e) means for obtaining a plurality of linear radioactivity densities each corresponding to an image point on said at least one planar image within said image volume; and f) means for multiplying said plurality of linear radioactivity densities by said image volume to obtain total radioactivity of said image volume.

5. An apparatus for determining internal radioactivity and/or absorbed dose estimates of claim 4, further comprising:

a) means for simulating in a computer an infinite homogeneous soft tissue medium having a predetermined mass density;

b) means for subdividing a predetermined area of said tissue medium into a 3-dimensional voxel matrix, wherein the dimensions of said voxel matrix are the same as the dimensions of said image volume;

c) means for simulating a total energy deposition of a uniform unit of radiation energy from a source voxel to a plurality of neighboring voxels within said voxel matrix to determine an amount of energy deposited in each of said neighboring voxels;

d) means for obtaining an average dose in each of said neighboring voxels by dividing said energy deposited in each of said neighboring voxels by a corresponding mass of each one of said plurality of voxels;

e) means for dividing said total radioactivity of said image volume by a total number of voxels in said image volume to obtain a uniform activity concentration for each voxel of said image volume;

f) means for calculating a voxel source kernel for said simulated homogeneous tissue medium;

g) means for averaging doses of each one of said voxels in image volume to obtain an average absorbed dose of said image volume; and h) means for convoluting said voxel kernel with said image volume to obtain a dose for said image volume.

6. An apparatus for determining internal radioactivity and/or absorbed dose estimates of claim 5, further comprising means for generating statistical information as to spatial dose distribution of said image volume by using at least said average absorbed dose.

7. A computer program product having a computer readable medium having computer readable code recorded thereon for determining internal radioactivity and/or absorbed dose estimates, said computer readable code comprising:

a) means for obtaining a first plurality of tomographic images of a patient;

b) means for circumscribing at least one region of interest on at least one of said first plurality of tomographic images to obtain an image volume;

c) means for obtaining at least one planar image of said patient corresponding to a radioactivity distribution field within said patient;

d) means for fusing said image volume with said at least one planar image;

e) means for obtaining a plurality of linear radioactivity densities each corresponding to an image point on said at least one planar image within said image volume; and f) means for multiplying said plurality of linear radioactivity densities by said image volume to obtain total radioactivity of said image volume.

8. A computer program product having a computer readable medium having computer readable code recorded thereon for determining internal radioactivity and/or absorbed dose estimates of claim 7, said computer readable code further comprising:

a) means for simulating in a computer an infinite homogeneous soft tissue medium having a predetermined mass density;

b) means for subdividing a predetermined area of said tissue medium into a 3-dimensional voxel matrix, wherein the dimensions of said voxel matrix are the same as the dimensions of said image volume;

c) means for simulating a total energy deposition of a uniform unit of radiation energy from a source voxel to a plurality of neighboring voxels within said voxel matrix to determine an amount of energy deposited in each of said neighboring voxels;

d) means for obtaining an average dose in each of said neighboring voxels by dividing said energy deposited in each of said neighboring voxels by a corresponding mass of each one of said plurality of voxels;

e) means for dividing said total radioactivity of said image volume by a total number of voxels in said image volume to obtain a uniform activity concentration for each voxel of said image volume;

f) means for calculating a voxel source kernel for said simulated homogeneous tissue medium;

g) means for averaging doses of each one of said voxels in image volume to obtain an average absorbed dose of said image volume; and h) means for convoluting said voxel kernel with said image volume to obtain a dose for said image volume.

9. A computer program product having a computer readable medium having computer readable code recorded thereon for determining internal radioactivity and/or absorbed dose estimates of claim 8, said computer readable code further comprising means for generating statistical information as to spatial dose distribution of said image volume by using at least said average absorbed dose.

* * * * *